(12) United States Patent
Arne'

(10) Patent No.: US 8,394,016 B1
(45) Date of Patent: Mar. 12, 2013

(54) ILLUMINATED AIRWAY ARTICLE

(75) Inventor: Bruce Cabot Arne', Wilmington, NC (US)

(73) Assignee: Bruce Cabot Arné, Wilmington, NC (US)

( * ) Notice: Subject to any disclaimer, the term of this patent is extended or adjusted under 35 U.S.C. 154(b) by 922 days.

(21) Appl. No.: 12/496,704

(22) Filed: Jul. 2, 2009

(51) Int. Cl.
*A61B 1/267* (2006.01)

(52) U.S. Cl. ........................................... 600/193

(58) Field of Classification Search .............. 600/185, 600/190, 191, 192, 193, 199
See application file for complete search history.

(56) References Cited

U.S. PATENT DOCUMENTS

| | | | |
|---|---|---|---|
| 3,454,898 A | 7/1969 | Comstock | |
| 3,787,693 A | 1/1974 | Stone | |
| 3,826,248 A * | 7/1974 | Gobels | 600/193 |
| 3,833,805 A | 9/1974 | Naiman et al. | |
| 3,867,764 A | 2/1975 | Dunmire et al. | |
| 4,079,534 A | 3/1978 | Snyder | |
| 4,101,957 A | 7/1978 | Chang | |
| 4,129,780 A | 12/1978 | Laughlin | |
| 4,226,529 A | 10/1980 | French | |
| 4,266,873 A | 5/1981 | Hacskaylo et al. | |
| 4,293,892 A | 10/1981 | Plummer | |
| 4,315,150 A | 2/1982 | Darringer et al. | |
| 4,561,775 A | 12/1985 | Patrick et al. | |
| 4,574,784 A | 3/1986 | Soloway | |
| 4,707,595 A | 11/1987 | Meyers | |
| 4,738,044 A | 4/1988 | Osterhout | |
| 4,853,529 A | 8/1989 | Meyers | |
| 4,866,730 A | 9/1989 | Szatmari et al. | |
| 4,916,713 A | 4/1990 | Gerber | |
| 4,991,183 A | 2/1991 | Meyers | |
| 5,200,838 A | 4/1993 | Nudelman et al. | |
| 5,542,904 A | 8/1996 | Heine et al. | |
| 5,743,849 A * | 4/1998 | Rice et al. | 600/186 |
| 5,800,344 A | 9/1998 | Wood, Sr. et al. | |
| 5,906,576 A | 5/1999 | Upsher | |
| 5,938,591 A | 8/1999 | Minson | |
| 6,350,235 B1 * | 2/2002 | Cohen et al. | 600/199 |
| 6,464,625 B2 | 10/2002 | Ganz | |
| 6,491,618 B1 | 12/2002 | Ganz | |
| 6,543,447 B2 | 4/2003 | Pacey | |
| 6,626,829 B1 * | 9/2003 | Skaggs | 600/190 |
| 6,655,377 B2 | 12/2003 | Pacey | |
| 6,676,598 B2 | 1/2004 | Rudischhauser et al. | |
| 6,890,346 B2 | 5/2005 | Ganz et al. | |
| 6,916,105 B2 | 7/2005 | Zerphy et al. | |

(Continued)

OTHER PUBLICATIONS

Architectural and Engineering Specification for Infrared LED Illuminator, copyright Dec. 1999, E1DA0115-001, Rev E, pp. 1-8.

(Continued)

*Primary Examiner* — Kevin T Truong
*Assistant Examiner* — Michael Araj
(74) *Attorney, Agent, or Firm* — Smith Moore Leatherwood LLP; Clara R. Cottrell (57) ABSTRACT

An illuminated airway article adapted for use in opening an airway passage, said article comprising an elongated body having a distal end, wherein the distal end is adapted for contacting tissue of said airway passage, and a proximal end, at least two light sources affixed to said article wherein at least one of said light sources is an infrared light-emitting diode transmitting infrared light in the range of about 750 nm to about 3000 nm and at least one of said light sources is a conventional light-emitting diode, at least one voltage source electrically coupled to the light sources, and at least one means for activating the light sources.

19 Claims, 7 Drawing Sheets

U.S. PATENT DOCUMENTS

| | | |
|---|---|---|
| 6,986,739 B2 | 1/2006 | Warren et al. |
| 7,052,456 B2 | 5/2006 | Simon |
| 7,433,116 B1 | 10/2008 | Islam |
| 2003/0195390 A1 | 10/2003 | Graumann |
| 2005/0251119 A1 | 11/2005 | Eaton et al. |
| 2008/0208006 A1 | 8/2008 | Farr |
| 2008/0300475 A1 | 12/2008 | Jaeger et al. |
| 2008/0312507 A1 | 12/2008 | Kim |

OTHER PUBLICATIONS

Stephen Brock Blankenship, et al., "Tactical Emergency Medicine: Emerging Technologies for the Tactical Medical Provider," copyright 2008, Tactical Emergency Medicine, book, Chapter 35, pp. 240-252, Richard B. Schwartz, et al., ed.

Robert T. Gerhardt, "Tactical En Route Care," copyright 2008, Tactical Emergency Medicine, book, Chapter 21, pp. 153-167, Richard B. Schwartz, et al., ed.

James A. Harrington, "Infrared Fiber Optics," date unknown, pp. 1-3 and 10, Ceramic and Materials Engineering, Rutgers University, Piscataway, NJ, US.

Richard B. Schwartz, William L. Gillis, and Richard J. Miles, "Orotrachial Intubation in Darkness Using Night Vision Goggles," copyright Nov. 2001, Military Medicine, vol. 166, pp. 984-986.

The Electromagnetic Spectrum, web page, copyright Mar. 2009, National Aeronautics and Space Administration.

Jeff Tyson, "How Night Vision Works," web page, copyright Mar. 2009.

"Whats New?" web page, www.MedSchoolSupply.com, copyright Mar. 2009, Pro-Physician True View™ Fiberoptic LED Laryngoscope Set, www.laryngoscope.us.

\* cited by examiner

ILLUMINATED AIRWAY ARTICLE

The present invention is directed towards an illuminated airway article adapted for use in opening an airway passage.

BACKGROUND OF THE INVENTION

In a medical situation, whether in a hospital, the side of a road, or on the battlefield, a medical responder has certain procedures and tools at his or her disposal to stabilize the patient and increase the odds of survival. One of the procedures available to the medical responder is opening an airway for the patient. Securing an airway which can be used to support ventilation has been called "the primary requirement for patient survival" in military situations. Robert Gerhardt, Tactical En Route Care, Richard B. Schwartz, ed., 156 (2008). If the patient must be moved, the airway should be secured beforehand to mitigate complications that may arise during transport. Id.

The procedure itself can take different forms depending on the situation and injuries sustained by the patient. A laryngoscope is one of the tools available to the medical responder to open an airway for the patient without surgery. A laryngoscope usually has a light which illuminates the inside of the mouth and throat of the patient to assist the medical responder in its proper use.

SUMMARY

An illuminate airway article adapted for use in opening an airway passage comprising an elongated body with a distal end and a proximal end, at least two light sources, one of which is an infrared light-emitting diode transmitting infrared light in the range of about 750 nm to about 3000 nm and the other is a conventional light-emitting diode, at least one voltage sources coupled to the light sources, and at least one means for activating the light sources

DETAILED DESCRIPTION

The present invention is an illuminated airway article, such as a laryngoscope, that is used in opening the airway passage of the patient. The Applicant contemplates that the article may be waterproof or water resistant. Waterproof refers to the article being impermeable to water. Water resistance refers to the article being permeable to water minimally or only under certain conditions, such as prolonged emersion in water or other fluid.

Figure 1A:
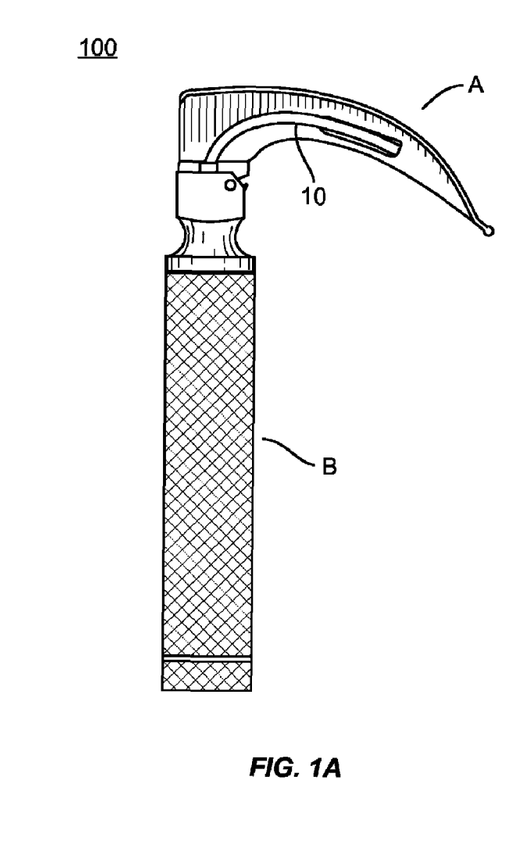
FIG. 1A is a perspective view of an article made in accordance with an embodiment of the present invention.
Figure 1B:
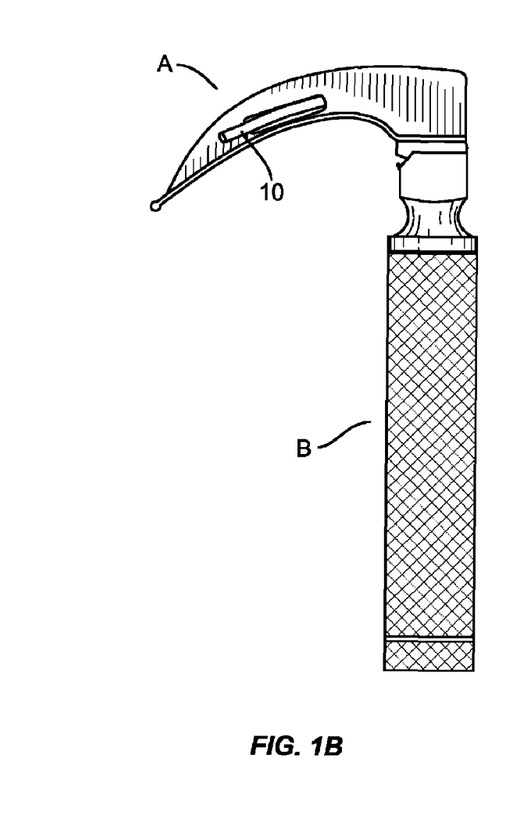
FIG. 1B is a perspective view of an article made in accordance with an embodiment of the present invention.

Turning now to FIGS. 1A and 1B, the article is composed of an elongated body having a distal end A and a proximal end B. The article may be formed as one unitary body or may be formed as individual pieces, such as a distal end A and proximal end B, which are then assembled to create the article. Applicant contemplates that the article may be coated with a non-reflective coating. Applicant also contemplates that the article may be made of a black or dark-colored material, or be painted, coated, or otherwise treated to make the article appear to be black or dark-colored. It is contemplated that the entire article could be made of metal, polymers, and/or derivatives and combinations thereof.

Figure 2:
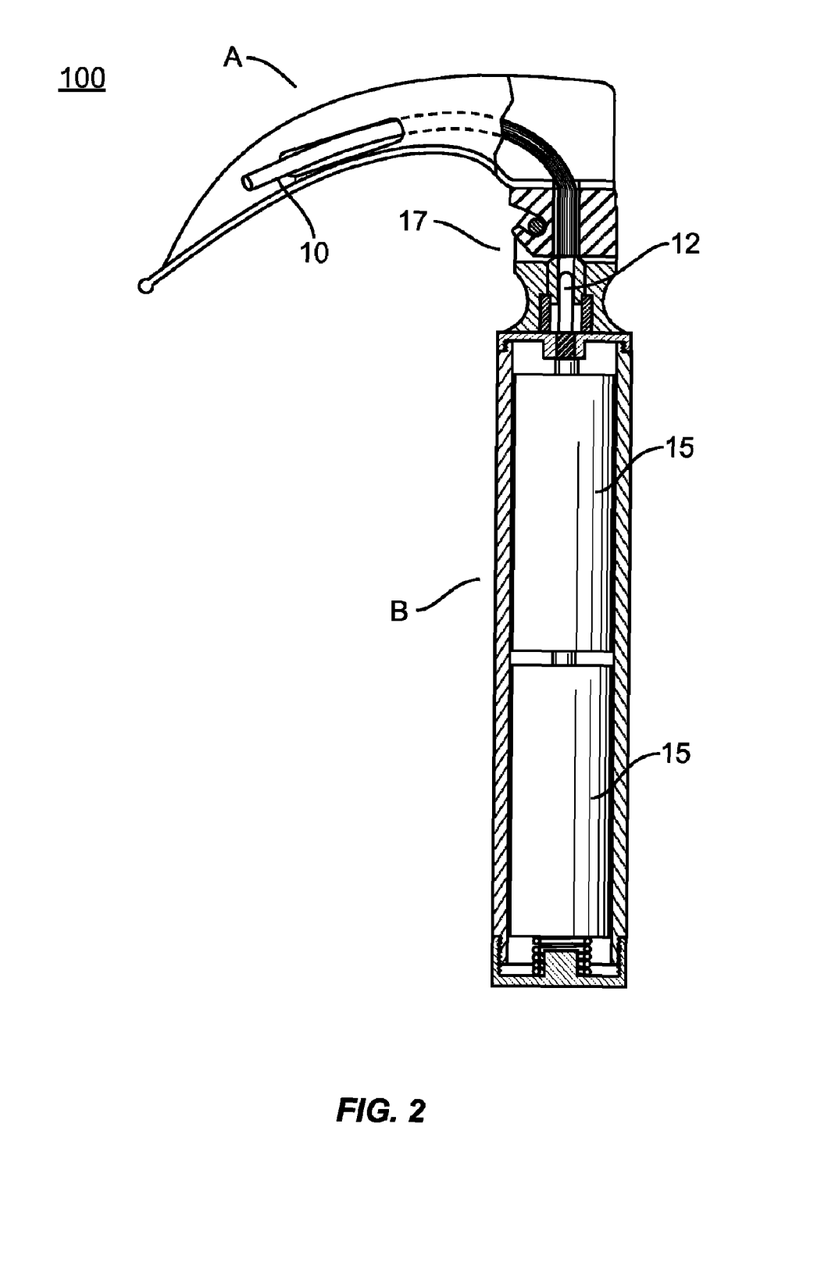
FIG. 2 is a cross-sectional view of the article set forth in FIG. 1A and FIG. 1B.
Figure 3A:
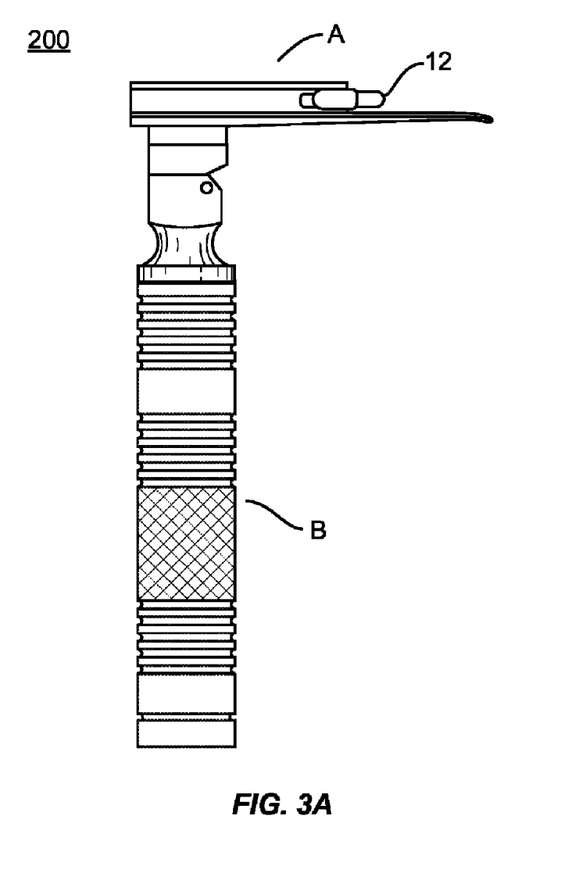
FIG. 3A is a perspective view of an article made in accordance with another embodiment of the present invention.
Figure 3B:
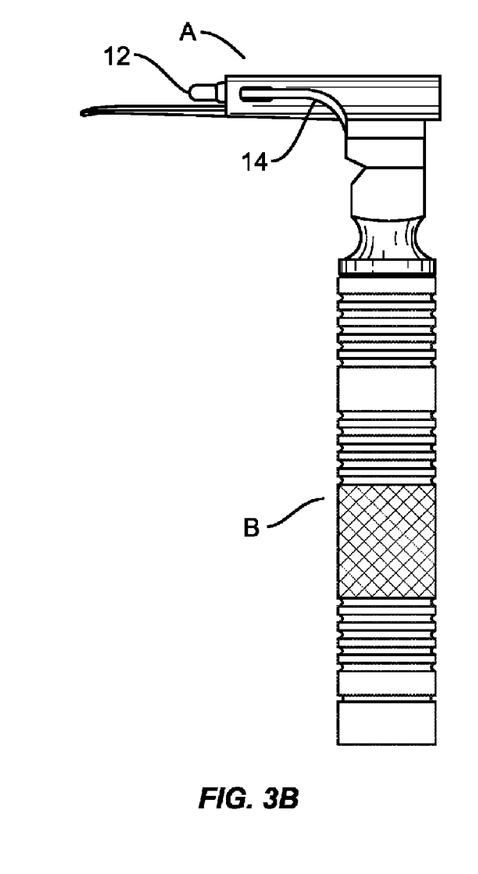
FIG. 3B is a perspective view of an article made in accordance with another embodiment of the present invention.
Figure 4:
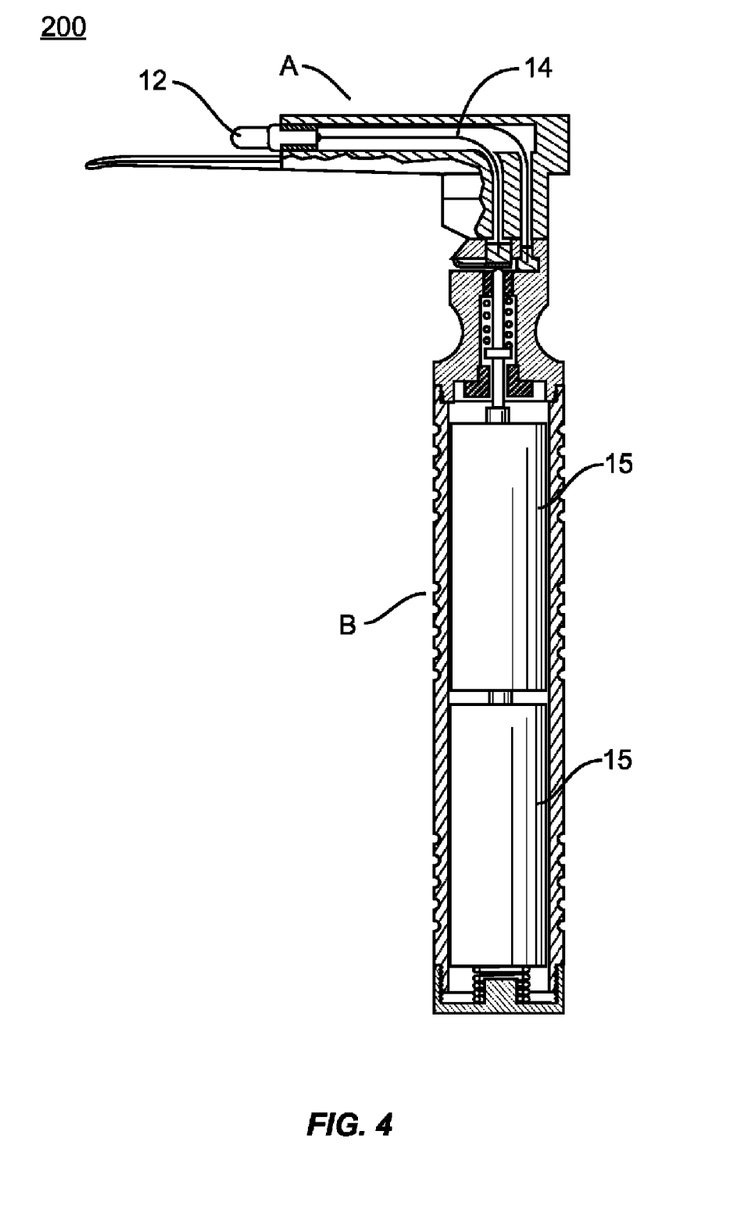
FIG. 4 is a cross-sectional view of the article set forth in FIG. 3A and FIG. 3B.

The proximal end B is generally adapted for gripping the article. To facilitate the gripping, the proximal end B may be textured, such as knurled, grooved, knobbed, roughed, pebbled, other such textures that those having skill in the art would appreciate as facilitating the handling of the article or combinations thereof as shown in FIGS. 1A, 1B, 3A and 3B. The proximal end B may be adapted to house a voltage source 15 such as a battery or series of batteries as shown in FIGS. 2 and 4. In one embodiment, the proximal end B may be in communication with one or more voltage sources located outside of the article (not shown) such as an electrical outlet, generator, or other source of power sufficient to power the light sources 12 found on the article. Applicant contemplates that the proximal end B may be coated with a non-reflective coating. Applicant also contemplates that the proximal end B may be made of a black or dark-colored material, or be painted, coated, or otherwise treated to make the proximal end B appear to be black or dark-colored.

Figure 6A:
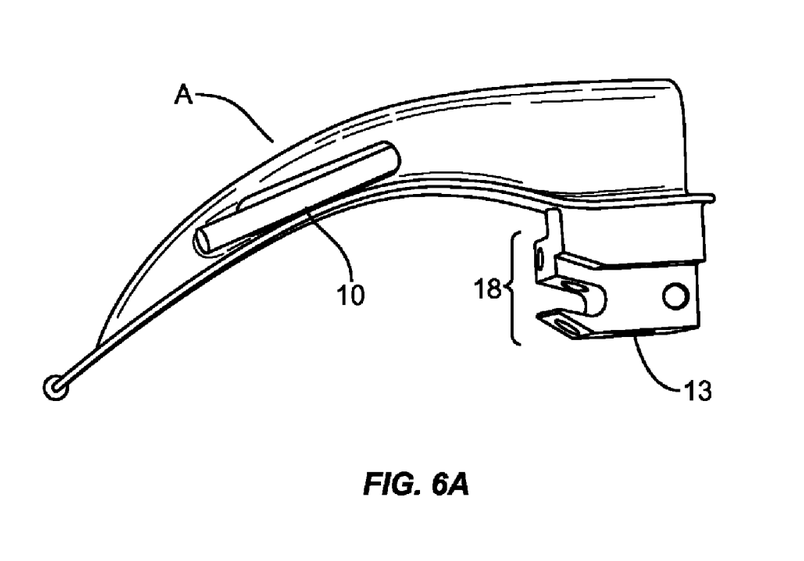
FIG. 6A is a perspective view of an element of an article made in accordance with an aspect of an embodiment of the present invention.
Figure 6B:
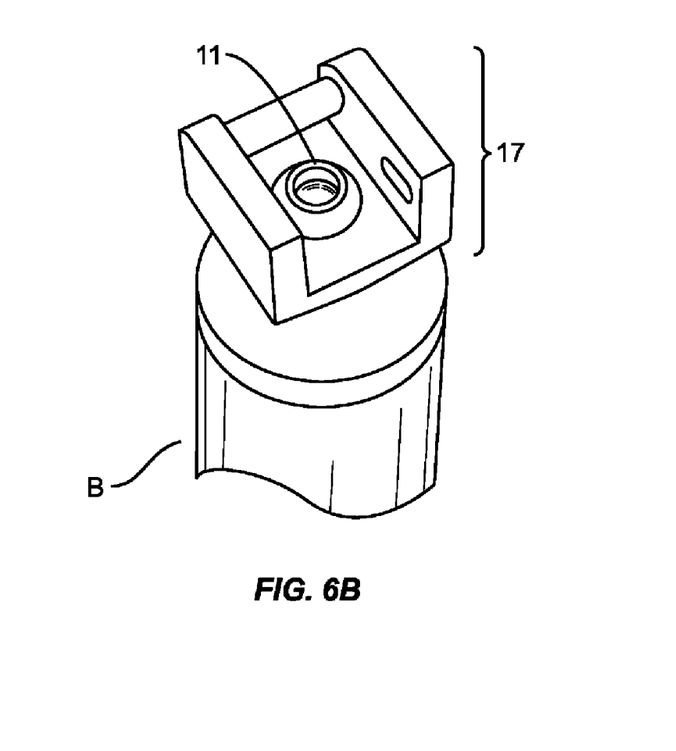
FIG. 6B is a perspective view of an element of an article made in accordance with an aspect of an embodiment of the present invention.
Figure 7A:
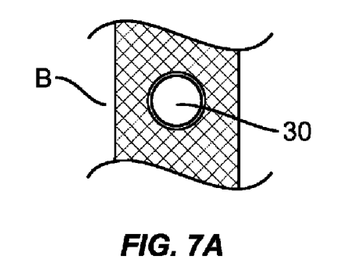
FIG. 7A is an illustrative view of an aspect of an article made in accordance with an aspect of an embodiment of the present invention.
Figure 7B:
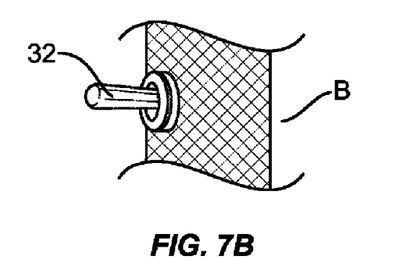
FIG. 7B is an illustrative view of an aspect of an article made in accordance with an aspect of an embodiment of the present invention.
Figure 7C:
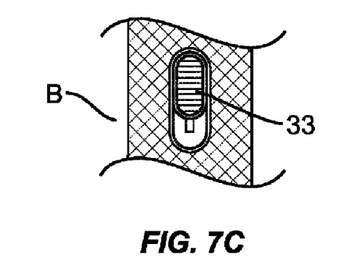
FIG. 7C is an illustrative view of an aspect of an article made in accordance with an aspect of an embodiment of the present invention.
Figure 7D:
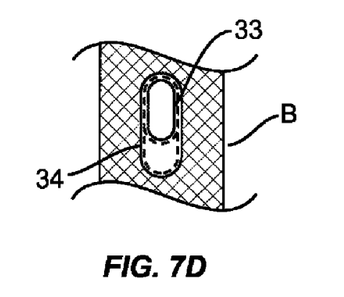
FIG. 7D is an illustrative view of an aspect of an article made in accordance with an aspect of an embodiment of the present invention.
Figure 7E:
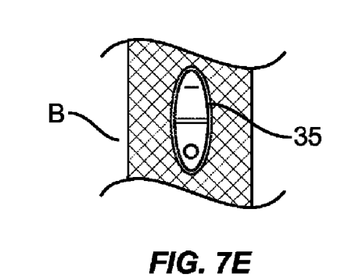
FIG. 7E is an illustrative view of an aspect of an article made in accordance with an aspect of an embodiment of the present invention.
Figure 7F:
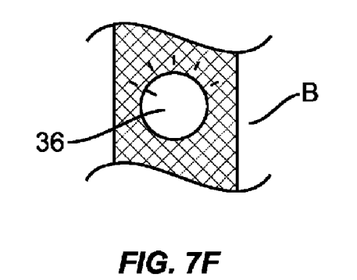
FIG. 7F is an illustrative view of an aspect of an article made in accordance with an aspect of an embodiment of the present invention.

The distal end A is contemplated as being adapted to contact the tissue of the airway passage that is being opened by the article. The distal end A may be removable, one example of which is shown in FIG. 6A. In such an embodiment, distal end A may be adapted 18 to facilitate the attachment and disentachment of the distal end A from proximal end B. In such an embodiment, the proximal end B may be adapted to facilitate 17 the attachment and disentachment of the distal end A 17, one example of which is shown in FIG. 6B. In one embodiment, Applicant contemplates that the portion of the distal end A which makes contact with the airway passage may be disposable. Applicant contemplates that the distal end A may be one or more blades known to those in the art as shown in FIG. 6A. Examples of such blades include, but are not limited to, Macintosh, as shown in FIGS. 1A and 1B, Miller, as shown in FIGS. 3A and 3B, Wisconsin, all of which may be of the American or English profile, as well as Phillips, Schapira, and Robertshaw blades, and modifications to the blades such as Cranwall and Siker, as well as other blades and modifications known to those having ordinary skill in the art. As would be known to one having ordinary skill in the art, these blades may be of different sizes to be used according to the size of the patient. Applicant contemplates that the distal end A may be coated with a non-reflective coating. Applicant also contemplates that the distal end A may be made of a black or dark-colored material, or be painted, coated, or otherwise treated to make the distal end A appear to be black or dark-colored.

Figure 5:
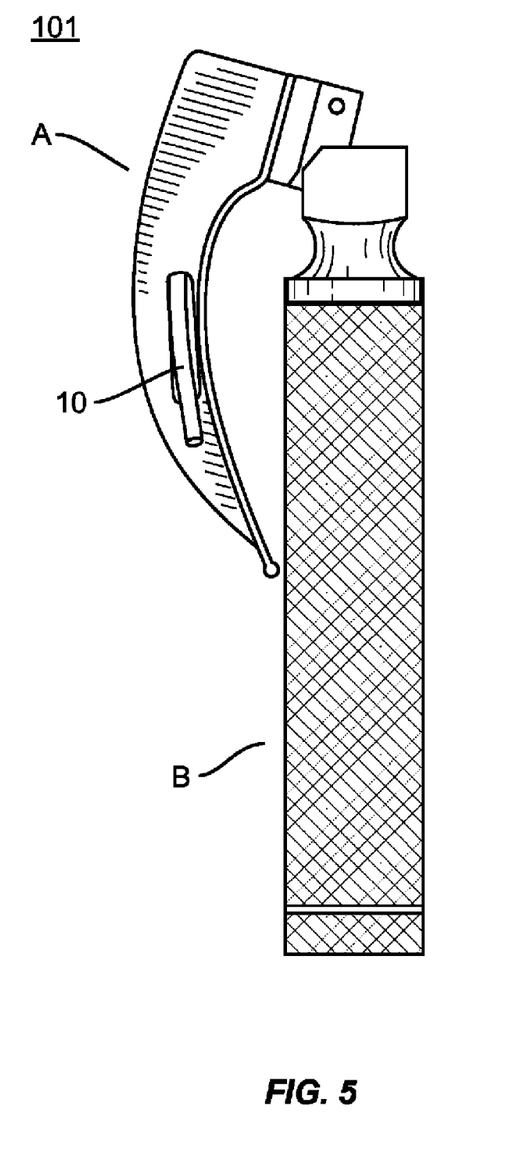
FIG. 5 is a perspective view of an article made in accordance with an aspect of an embodiment of the present invention.

The distal end A may be adapted to contact tissue of an airway passage when it is in the active position 100, 200, as shown in FIGS. 1A, 1B, 3A and 3B. When the article is in the inactive position 101, as shown in FIG. 5, the distal end A may not be in a position to contact the airway passage. In an embodiment of the article where the distal end A may be moved between an active position 100, 200 and an inactive position 101, the distal end A and the proximal end B may be adapted to facilitate the movement of light and/or the movement of voltage from the proximal end B to the distal end A. As shown in FIG. 6B, this adaptation may be a node 11 on the proximal end B at the point the distal end A makes contact with the proximal end B in an active position 100, 200. The node 11 may be the end of fiber optic 10 or a conduit through which voltage from the voltage source 15 may pass from the proximal end B to the distal end A. More specifically, the voltage from the voltage sources 15 may pass to the light sources 12 located on the distal end A in an embodiment where the light sources 12 are located on the distal end A.

Article 200 shows a light-emitting diode ("LED") 12, wherein a LED is a semiconductor diode that emits light when voltage is applied, at the distal end A of the article. Applicant contemplates that the article may comprise at least two light sources 12 which may be at least two LEDs. One of the LEDs may transmit infrared light in the range of about 750 nanometers to about 3000 nanometers. At least one of the other LEDs may transmit conventional or white light. In an aspect of the embodiment, the infrared LED may transmit infrared light in the range of about 900 nanometers to about 3000 nanometers. In another aspect of the embodiment, the infrared LED may transmit infrared light in the range of about 900 nanometers to about 1500 nanometers. In another aspect of the embodiment, the infrared LED may transmit infrared light in the range of about 1500 nanometers to about 3000 nanometers. In another aspect of the embodiment, the infrared LED may transmit infrared light in the range of about 1000 nanometers to about 2000 nanometers. Applicant contemplates that the infrared LED will transmit infrared light in a range which is not visible to the naked eye. Applicant contemplates that the LED transmitting infrared light will not transmit infrared light above about 30,000 nanometers. Applicant contemplates that the infrared light will be visible to one utilizing night vision devices such as, but not limited to, scopes, goggles, and cameras. Generally, such night vision devices "use cathode ray tubes to amplify ambient light to levels more easily detected by the human eye." Stephen Brock Blankenship, et al., Tactical Emergency Medicine: Emerging Technologies for the Tactical Medical Provider, Richard B. Schwartz, et al., ed., 244 (2008). The night vision devices may also use infrared illuminators in addition to or instead of the infrared illumination provided by the article via the infrared LED light source 12.

The light sources 12 may be located on the distal end A of the article, as shown in FIGS. 3A and 3B. The light sources 12 may also be affixed to the article at the proximal end B as shown in FIGS. 1A and 1B. If the light source 12 is affixed at the proximal end B, the article may comprise fiber optics 10 affixed between the light source 12 and the distal end A of the article such that the light, conventional, infrared, or other light source, is directed out of the fiber optic 10 at the distal end A as shown in FIGS. 1A and 1B. Applicant contemplates that other means as known to one having ordinary skill in the art for transmitting the light from the light source 12 at the proximal end B to the distal end A may be used. In a further embodiment, Applicant contemplates that the light sources 12 may be located both on the distal end A and the proximal end B (not shown) of the article. For example, the infrared light source 12 may be located on the distal end A, whereas the conventional light source 12 may be located at the proximal end B and be in communication with the distal end A via fiber optics 10 or some other means of allowing the light transmitted by the conventional light source 12 to move from the proximal end B to the distal end A. Conversely, the conventional light source 12 may be located on the distal end A whereas the infrared light source 12 is located on the proximal end B and be in communication with the distal end A via fiber optics 10 or some other means of allowing the light transmitted by the infrared light source 12 to move from the proximal end B to the distal end A.

The article further comprises at least one means for activating the light sources 12. The means for activating or inactivating the light sources 12 may be a switch. Examples, as shown in FIGS. 7A-7F, of suitable switches include, but are not limited to, single-pole switches, double-pole switches, single-pole and double-pole switches with various combinations of throws, push button 30, toggle switch 32, slide switch 33, rocker switch 35, a position switch 36, a switch such as a slide switch 33 covered by a soft waterproof or water resistant polymer sheet 34, other switches known to one having ordinary skill in the arts, or any combination thereof.

Applicant contemplates that the means for activating and deactivating the light source 12 or sources may be waterproof or water resistant as discussed above. The waterproof and/or water resistant nature of the means for activating or deactivating the light sources 12 may be accomplished through the use of gaskets, O-rings, polymeric coatings or sheets 34, chemical coatings, mechanical apparatus, combinations thereof, or other means of waterproofing and/or making water resistant known to those having ordinary skill in the art. The article may comprise more than one means for activating and inactivating the light sources 12. For example, one means may activate the infrared LED only, whereas another means may activate the conventional light source only. Applicant contemplates that an additional means could be located on the article to deactivate all of the light sources 12 on the article. Applicant contemplates an embodiment where there is only one means for activating the conventional light source 12 and the infrared light source 12 as well as deactivating both the conventional light source 12 and the infrared light source 12. Applicant contemplates a method for activating the infrared light source 12 wherein the infrared light source 12 is activated when the distal end A is moved from the inactive position 101, as shown in FIG. 5, to the active position 100, 200, as shown in FIGS. 1A, 1B, 3A, and 3B. In one embodiment, Applicant contemplates an embodiment such as described where the infrared light source 12 is activated when the distal end A is moved from the inactive position 101 to the active position 100, 200, further comprising a means for activating and deactivating the conventional light source 12 separate from the means of activating and deactivating the infrared light source 12. Applicant contemplates an embodiment such as described infrared light source 12 is activated when the distal end A is moved from the inactive position 101 to the active position 100, 200 further comprising an additional means which would deactivate the infrared light source 12 when the distal end A is in the active position 100, 200. Applicant contemplates an embodiment of the present invention where there are two means for activating and deactivating the light sources 12, such that one means activates and deactivates the infrared light source 12 and the other means activates and deactivates the conventional light source 12 or some other light source 12. Applicant contemplates an embodiment in which such means for activating and deactivating the infrared light source 12 or such means for activating and deactivating the conventional light source 12 is a push button 30, toggle 32, or other such means where it is not apparent from the position of the switch which light source 12 will be activated, or if either light source is activated, that the means be biased to the infrared light source 12 such that the infrared light source 12 will be activated upon initiation of the means such as pushing the push button 30 or toggling the toggle switch 32. Applicant also contemplates an embodiment of the article wherein the article will default to the infrared light source 12 when activated and another means must be used to deactivate the infrared light source 12, or activate and/or deactivate the conventional light source 12. In addition, Applicant contemplates that there may be a means for deactivating the infrared light source 12 once the article has defaulted to the infrared light and/or a means for activating or deactivating the conventional light source 12 while the infrared light source 12 is activated or deactivated. In one aspect of the embodiment of the article, Applicant contemplates a position switch or knob 36 where the different positions of the switch include, but are not limited to, activating the infrared light source 12, deactivating the infrared light source 12, activating the conventional light source 12, deactivating the conventional light source 12, or any combination thereof such as activating the infrared light source 12 and deactivating the conventional light source 12 in one position or deactivating the infrared light source 12 and activating the conventional light source 12 in another position. Applicant contemplates an embodiment of the present article wherein moving the distal end A to the active position 100, 200 from the inactive position 101 initiates the voltage sources 15 such that only in the active position can the means for inactivating or deactivating the light sources 12 be used. Applicant contemplates a combination of different means for activating the infrared and conventional light sources 12 such as using a push button switch 30 to activate the infrared light source 12 and a slide switch 33 for activating or deactivating the conventional light source 12. Another such example is the infrared light source 12 being activated when the distal end A is moved from the inactive position 101 to the active position 100, 200, and another means located on the proximal end B such as a slide switch 33 or rocker switch 35 being used to activate or deactivate the conventional light source 12. Applicant contemplates that the different means to activate and deactivate the infrared and conventional light sources 12 may be located on any position on the proximal end B.

Certain modifications and improvements will occur to those skilled in the art upon a reading of the foregoing description. All such modifications and improvements of the present invention have been deleted herein for the sake of conciseness and readability.

Numerous other aspects of embodiments, embodiments, features, and advantages of the present invention will appear from the description and the accompanying drawings. In the description and/or the accompanying drawings, reference is made to exemplary aspects of embodiments and/or embodiments of the invention, which may be applied individually or combined in any way with each other. Such aspects of embodiments and/or embodiments do not represent the full scope of the invention.

What is claimed is:

1. An illuminated airway article adapted for use in opening an airway passage, said article comprising:
    an elongated body having a distal end and a proximal end;
    at least two light sources affixed to said article;
    at least one voltage source electrically coupled to said at least two light sources; and
    at least one means for activating said at least two light sources;
    wherein said distal end is adapted for contacting tissue of said airway passage; and
    wherein at least one of said light sources is an infrared light-emitting diode transmitting infrared light in the range of about 750 nm to about 3000 nm;
    wherein at least one of said light sources is a conventional light-emitting diode; and
    wherein said means for activating said light sources is configured to activate said infrared light-emitting diode prior to the activation of said conventional light-emitting diode.

2. The article according to claim 1, wherein said infrared light-emitting diode transmits infrared light in the range of about 900 nm to about 3000 nm.

3. The article according to claim 1, said distal end comprising one or more blades.

4. The article according to claim 3, wherein said blades are removable.

5. The article according to claim 3, wherein said blades are disposable.

6. The article according to claim 3, wherein said means for activating said light sources comprises moving said blade into a position wherein said blade is in a position for use.

7. The article according to claim 6, wherein said means for activating said light sources activates said infrared light-emitting diode.

8. The article according to claim 1, wherein said means for activating said light sources is affixed to said handle.

9. The article according to claim 1, wherein said means for activating said at least two light sources is configured to bias to said infrared light-emitting diode.

10. The article according to claim 1, further comprising at least two means for activating said light sources;
    wherein one of said means is configured to activate said infrared light-emitting diode; and
    wherein one of said means is configured to activate said conventional light-emitting diode.

11. The article according to claim 1, wherein said at least one means for activating said at least two light sources is configured to default to inactivate said at least two light sources.

12. The article according to claim 1, wherein said at least one means for activating said at least two light sources is configured to activate one of said light sources, to activate the other of said light sources, and to inactivate all of said light sources.

13. The article according to claim 1, wherein said at least two light sources are affixed to said distal end.

14. The article according to claim 1, further comprising fiber optics;

wherein at least one of said at least two light sources are located at said proximal end; and wherein said fiber optics are in communication with said at least one of said at least two light sources and with said distal end.

15. The article according to claim 1, wherein said voltage source is located at said proximal end.

16. The article according to claim 1, wherein said voltage source is in communication with said proximal end.

17. The article according to claim 1, wherein said proximal end is textured.

18. The article according to claim 1, wherein said article is finished in a non-reflective coating.

19. The article according to claim 1, wherein said article is water resistant or water proof.

* * * * *